(12) United States Patent
Zink

(10) Patent No.: US 11,892,531 B2
(45) Date of Patent: Feb. 6, 2024

(54) MAGNETIC RESONANCE ANTENNA WITH WIRE STRUCTURE EMBEDDED IN FOAM

(71) Applicant: Siemens Healthcare GmbH, Erlangen (DE)

(72) Inventor: Stephan Zink, Bayern (DE)

(73) Assignee: Siemens Healthcare GmbH, Erlangen (DE)

(*) Notice: Subject to any disclaimer, the term of this patent is extended or adjusted under 35 U.S.C. 154(b) by 29 days.

(21) Appl. No.: 17/407,309

(22) Filed: Aug. 20, 2021

(65) Prior Publication Data

US 2022/0057460 A1 Feb. 24, 2022

(30) Foreign Application Priority Data

Aug. 21, 2020 (DE) .................... 10 2020 210 645.2

(51) Int. Cl.
*G01R 33/34* (2006.01)
*G01R 33/00* (2006.01)
*G01R 33/341* (2006.01)
*A61B 5/055* (2006.01)

(52) U.S. Cl.
CPC ... *G01R 33/34038* (2013.01); *G01R 33/0052* (2013.01); *G01R 33/341* (2013.01); *A61B 5/055* (2013.01)

(58) Field of Classification Search
CPC .......... G01R 33/34038; G01R 33/0052; G01R 33/341; A61B 5/055
See application file for complete search history.

(56) References Cited

U.S. PATENT DOCUMENTS

| 6,169,401 | B1* | 1/2001 | Fujita | G01R 33/3678 |
| | | | | 324/318 |
| 6,313,633 | B1* | 11/2001 | Boskamp | G01R 33/34053 |
| | | | | 324/318 |
| 2013/0241557 | A1 | 9/2013 | Wolf et al. | |
| 2017/0089991 | A1 | 3/2017 | Gruber et al. | |
| 2018/0284202 | A1 | 10/2018 | Biber | |
| 2018/0372817 | A1* | 12/2018 | Rahmat-Samii | ............................ |
| | | | | G01R 33/34084 |
| 2019/0154773 | A1* | 5/2019 | Stack | G01R 33/34084 |
| 2019/0277926 | A1* | 9/2019 | Stormont | G01R 33/3685 |
| 2019/0310329 | A1* | 10/2019 | Malik | A61B 5/055 |
| 2019/0353722 | A1* | 11/2019 | Stormont | G01R 33/3628 |

FOREIGN PATENT DOCUMENTS

| CN | 110090020 A | 8/2019 |
| DE | 102010024432 A1 | 12/2011 |
| DE | 102015218749 A1 | 3/2017 |

OTHER PUBLICATIONS

German Office Action for German Application No. 10 2020 210 645.2 dated Jun. 10, 2021.

* cited by examiner

*Primary Examiner* — Dixomara Vargas
(74) *Attorney, Agent, or Firm* — Lempia Summerfield Katz LLC

(57) ABSTRACT

Systems for a magnetic resonance antenna, an MR local coil, a magnetic resonance device, and a method of producing a magnetic resonance antenna. The magnetic resonance antenna includes at least one wire structure. The at least one wire structure is shaped such that an electrical voltage may be induced in the at least one wire structure by a magnetic resonance signal. The magnetic resonance antenna also includes at least one accommodating body in which the at least one wire structure is embedded, for example completely.

11 Claims, 7 Drawing Sheets

MAGNETIC RESONANCE ANTENNA WITH WIRE STRUCTURE EMBEDDED IN FOAM

CROSS REFERENCE TO RELATED APPLICATIONS

This patent document claims the benefit of DE 102020210645.2 filed on Aug. 21, 2020 which is hereby incorporated in its entirety by reference.

FIELD

Embodiments relate to a magnetic resonance (MR) antenna, an MR local coil, a magnetic resonance device and a method for producing a magnetic resonance antenna.

BACKGROUND

In medical technology, magnetic resonance tomography, also known as magnetic resonance imaging (MRI), is characterized by high soft tissue contrast. In this process, excitation pulses are radiated into an examination subject, that is usually a patient, using a magnetic resonance device. This triggers magnetic resonance signals in the patient. The magnetic resonance signals are received as scan data by the magnetic resonance device and used to reconstruct magnetic resonance images.

The magnetic resonance signals are often received using so-called local coils, that are commonly also called surface coils. The local coils are usually placed in close proximity to the patient in order to achieve a high signal-to-noise ratio of the received magnetic resonance signals.

In order to mold the local coil to the patient, it should be as light and flexible as possible. To achieve high flexibility of the local coil, magnetic resonance antennas incorporated therein should also be as flexible as possible. Conventional antennas include flexible printed circuit boards as substrate material, on which thin copper traces are applied. For this purpose, a copper layer is first applied to the substrate material and is subsequently etched away again in certain areas so that e.g., loop-shaped copper traces are produced. The copper traces are shaped in such a way that electrical voltages may be induced in the copper traces by a magnetic resonance signal.

However, the flexible printed circuit boards may break depending on the stress, especially bending, to which they are subjected. At intersection points of two copper traces, it is usually necessary to route one of the intersecting copper traces from one side of the PCB to the other, i.e., vias are used to provide a connection from one side to the other. In addition, the copper traces have only a very small spacing at the intersection points, so that undesirable capacitances may build up. The regions of the copper traces are therefore often made narrower in order to overlay less surface area. As a result, the copper traces may break easily.

BRIEF SUMMARY AND DESCRIPTION

The scope of the present invention is defined solely by the appended claims and is not affected to any degree by the statements within this summary. The present embodiments may obviate one or more of the drawbacks or limitations in the related art.

Embodiments provide a robust magnetic resonance antenna and a production method suitable for the manufacture thereof.

A magnetic resonance antenna for use in conjunction with a magnetic resonance device is provided. The antenna includes at least one wire structure. The at least one wire structure is shaped such that an electrical voltage may be induced in the at least one wire structure by a magnetic resonance signal. The magnetic resonance antenna also includes at least one accommodating body in which the at least one wire structure is embedded, for example completely.

The at least one wire structure may include at least one electrical conductor including at least one electrically conductive wire. If an electrical conductor includes a plurality of wires or cores, it may also be referred to as a stranded conductor. The material of the electrical conductor is e.g., copper. For example, the at least one wire structure is implemented as a cable. The at least one wire structure may include a single-core or multi-core composite of electrically conductive cores sheathed with an insulating material.

The at least one wire structure may be loop-shaped. For example, the loop may be in the shape of a circle, oval or figure-of-eight. The size of the wire structure may be configured to receive magnetic resonance signals. Magnetic resonance signals may be radiofrequency signals including a center frequency of between 10 and 500 MHz.

Each of the at least one wire structures may individually receive a magnetic resonance signal that may be transmitted to an evaluation unit of a magnetic resonance device via a respective receive channel. For example, a wire structure acts as a coil element and/or individual antenna. The magnetic resonance antenna may include, for example one, four, eight, 16, 32 or 64 wire structures or coil elements or individual antennas.

The at least one wire structure may include an interface via which the at least one wire structure may be connected to further electronic components, for example electronic assemblies, of the local coil, such as e.g., a preamplifier.

By using the at least one wire structure, the mechanical stability of the magnetic resonance antenna may be advantageously increased compared to conventional designs.

The accommodating body provides a safe distance from a patient so that the risk of excessive patient exposure, for example, is reduced.

The accommodating body may include a foam material, a felt material and/or a knitted fabric. The accommodating body includes a material that may be processed thermally and/or by bonding.

The foam material includes a cellular structure and/or gaseous inclusions. For example, the foam material may be a plastic such as e.g., polyethylene (PE) or polyurethane (PU).

The at least one wire structure is embedded, for example completely, in the carrier body. For example, the at least one wire structure is enclosed on all sides by the accommodating body, for example by the foam material. It is possible for the wire structure to be fixedly connected to the carrier body. It is also possible for the wire structure to be movable in the carrier body.

The at least one wire structure is advantageously protected from media such as e.g., water or disinfectant by the accommodating body. In addition, any intersection points of the at least one wire structure may be better implemented, so that the quality of the received magnetic resonance signals—and ultimately also of any magnetic resonance images created therefrom—may be improved.

The accommodating body makes it possible for example to implement functionalities such as sealing of housings, fastening of push buttons, padding of sharp edges, more and less bendable regions, etc.

The accommodating body and/or the at least one wire structure is advantageously flexible, for example bendable. This provides that the magnetic resonance antenna as a whole is also flexible and may be closely molded to the shape of a patient. The magnetic resonance antenna may be geometrically adjusted in a three-dimensional manner, i.e., may be bent about more than one axis.

One embodiment of the magnetic resonance antenna provides that the wire structure includes a single electrical line and/or an electrical coaxial line and/or an electrical triaxial line and/or an electrical sheathed multiple line.

Wire structures of this kind may be suitable for receiving magnetic resonance signals and may provide high dielectric and mechanical strength for a magnetic resonance antenna. In addition, they are advantageously available by the meter and do not require photochemical processing.

A single electrical line may be, for example, an electrical conductor, may be enclosed by an insulating material. A coaxial electrical line, for example a coaxial cable, usually includes an inner conductor and an outer conductor concentrically surrounding the inner conductor. The inner conductor and outer conductor are usually separated from one another by an insulating material (dielectric). A triaxial electrical line, for example a triaxial cable, typically includes an inner conductor, a first outer conductor and a second outer conductor. The second outer conductor concentrically surrounds the first outer conductor and the first outer conductor concentrically surrounds the inner conductor. The inner conductor and first outer conductor may be separated by a first insulating material. The first outer conductor and second outer conductor may be separated from one another by a second insulating material.

An electrical sheathed multiple line may include a plurality of electrical lines running parallel side by side, but not concentric with one another. This plurality of electrical lines may be surrounded by an outer conductor. An insulating material may be disposed between the plurality of inner electrical lines and the outer conductor.

According to another embodiment of the magnetic resonance antenna, the wire structure includes at least one capacitor, for example a shortening capacitor.

A shortening capacitor may be a capacitor used to electrically shorten antennas or more specifically the wire structure. A shortening capacitor is usually connected in series with the single antenna or wire structure or coil element and may be of the highest possible quality.

Another embodiment of the magnetic resonance antenna provides that the magnetic resonance antenna includes at least one component, fixedly connected to the accommodating body, for connecting an electronic component. Advantageously, any electronic components may thereby be easily and conveniently connected to the magnetic resonance antenna, for example in a detachable manner.

Another embodiment of the magnetic resonance antenna provides that the accommodating body is of planar design and has two opposing surfaces. The at least one wire structure is disposed centrally between the opposing surfaces.

A planar accommodating body enables the magnetic resonance antenna to be easily incorporated in a local coil that may be shaped to a patient like a blanket. The central position of the at least one wire structure ensures that it has an equal safety margin on both sides. Thus, a user of a local coil incorporating such a magnetic resonance antenna does not need to make sure which side of the local coil is facing the patient, so that the local coil may be used in an uncomplicated manner.

According to another embodiment of the magnetic resonance antenna, the accommodating body includes regions close to the at least one wire structure that have a lower density than regions remote from the at least one wire structure. The greater compression of the accommodating body, for example of the foam material, in the more remote regions provides the shape of the magnetic resonance antenna to be better retained.

For example, the distance between opposing surfaces close to those of the at least one wire structure is greater than locations more remote therefrom. For example, the foam material around the at least one wire structure is thicker than in regions farther away from the at least one wire structure.

In addition, the at least one wire structure may include a plurality of three-dimensionally shaped wire structures. The accommodating body with the wire structures disposed therein, for example centrally, is pre-formed for a specific body region (e.g., knee, chest or head). The magnetic resonance antenna is thus advantageously subject to less deformation stress during operation. As a result, the wire structures are also subjected to less stress.

A further embodiment of the magnetic resonance antenna provides that the regions of the accommodating body remote from the at least one wire structure include at least one aperture. This may be e.g., a hole and/or a recess and/or a cutout.

The at least one aperture may be used, for example, to fix the magnetic resonance antenna to other parts of a local coil, e.g., an outer skin or other layers. For example, snap fasteners or Velcro areas, etc. may also be used.

Larger apertures may also allow apertures on any outer skin of the local coil. Small apertures may be useful for internal wiring and/or may be suitable for increasing the flexibility of the antenna.

A local coil including at least one of the magnetic resonance antennas described above is also provided.

In addition to the magnetic resonance antenna, the local coil may include further components, such as one or more preamplifiers for amplifying a received magnetic resonance signal and/or a connecting cable for connecting the local coil to a magnetic resonance device.

One embodiment of the local coil provides that the local coil includes an outer skin. The at least one accommodating body included the at least one wire structure embedded therein is enclosed by the outer skin.

Further layers such as a padding layer and/or a sliding layer may be disposed between the outer skin and the at least one magnetic resonance antenna. A padding layer may improve the feel of the local coil. A sliding layer may provide that the layers disposed within the outer skin may move more easily relative to one another. For example, this may increase the flexibility of the local coil.

A magnetic resonance device including at least one of the local coils described above is also provided.

A method for producing a magnetic resonance antenna is also provided. The method includes the following steps: providing a sheet of, for example, foam material, making at least one slit in the sheet, placing at least one wire structure in the at least one slit, applying pressure and/or temperature to the sheet so that the at least one slit is sealed.

The advantages of the method for producing a magnetic resonance antenna essentially correspond to the advantages, as detailed above, of the proposed magnetic resonance antenna and local coil. Features, advantages or alternative embodiments mentioned in this connection may likewise be applied to the other claimed objects and vice versa.

For example, the object-related claims may also be further developed using the features described or claimed in connection with a method.

The profile of the at least one slit advantageously determines the shape of the at least one wire structure. The slit may be made e.g., using a blade, a punch, a laser and/or a milling machine.

The method provides a simple method of reproducing the design of the at least one wire structure in the accommodating body, since only the accommodating body, for example a foam material, is slit and the required wire is inserted. The wire structures, for example the types of wire of the wire structures, may be optimally matched to the respective application, so that compromises are minimized.

The sheet provided, for example of foam material, may include a thickness of between 5 to 15 mm prior to further processing, i.e., for example before the application of pressure and/or temperature.

After the at least one wire structure has been placed in the at least one slit and before pressure and/or temperature is applied, a liner, for example of foam material, may be applied to the surface of the sheet in which the at least one slit has been made. The application of the liner therefore results in a layered structure with the sheet as a first layer and the liner as a second layer. The application of the liner to the surface of the sheet may e.g., involve placing the liner onto the surface of the sheet.

The applied liner, for example made of foam material, may include a thickness of between 1 and 3 mm when applied.

By applying pressure and/or temperature to the sheet, the liner, for example of foam material, and the sheet, for example of foam material, may be bonded to form a homogeneous material composite.

Advantageously, the slit that has been made is closed particularly securely by the homogeneous material composite of liner and sheet.

DETAILED DESCRIPTION

Figure 1:
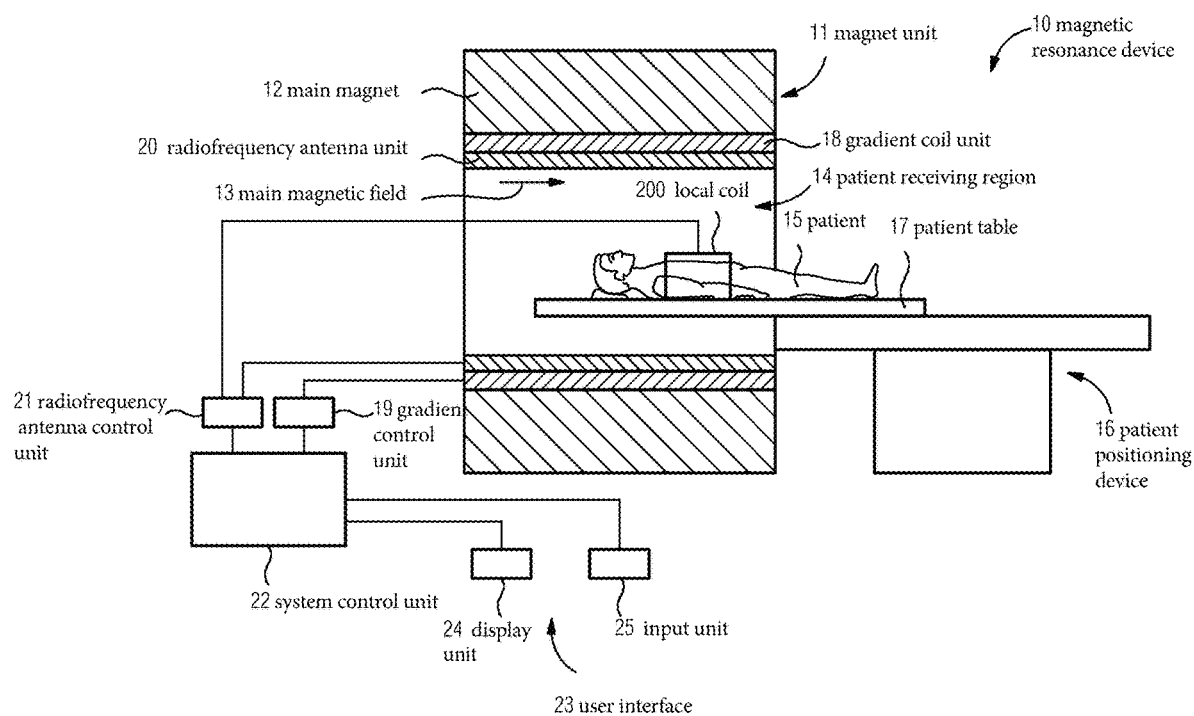
FIG. 1 depicts a magnetic resonance device with a local coil.

FIG. 1 schematically illustrates a magnetic resonance device 10. The magnetic resonance device 10 includes a magnet unit 11 including a main magnet 12 for generating a powerful and, for example, time-constant main magnetic field 13. In addition, the magnetic resonance device 10 includes a patient receiving region 14 for accommodating a patient 15. The patient receiving region 14 in this embodiment is cylindrical in shape and is cylindrically enclosed in a circumferential direction by the magnet unit 11. However, any configuration of the patient receiving region 14 differing therefrom is possible. The patient 15 may be slid into the patient receiving region 14 by a patient positioning device 16 of the magnetic resonance device 10. The patient positioning device 16 includes a patient table 17 that is configured to be movable within the patient receiving region 14.

The magnet unit 11 also includes a gradient coil unit 18 for generating magnetic field gradients that are used for spatial encoding during imaging. The gradient coil unit 18 is controlled by a gradient control unit 19 of the magnetic resonance device 10. The magnet unit 11 additionally includes a radiofrequency antenna unit 20 that in this embodiment is implemented as a body coil fixedly incorporated in the magnetic resonance device 10. The radiofrequency antenna unit 20 is controlled by a radiofrequency antenna control unit 21 of the magnetic resonance device 10, and radiates radiofrequency magnetic resonance sequences into an examination space that may be constituted by a patient receiving region 14 of the magnetic resonance device 10. This causes excitation of atomic nuclei to be imparted to the main magnetic field 13 generated by the main magnet 12. Relaxation of the excited atomic nuclei causes magnetic resonance signals to be generated. The radiofrequency antenna unit 20 is configured to receive the magnetic resonance signals.

The magnetic resonance device 10 includes a system control unit 22 for controlling the main magnet 12, gradient control unit 19, and for controlling the radiofrequency antenna control unit 21. The system control unit 22 centrally controls the magnetic resonance device 10, e.g., executing a predetermined imaging gradient echo sequence. The system control unit 22 additionally includes an evaluation unit (not shown in more detail) for evaluating the magnetic resonance signals acquired during the magnetic resonance examination. The magnetic resonance device 10 also includes a user interface 23 connected to the system control unit 22. Control information, such as imaging parameters, as well as reconstructed magnetic resonance images may be displayed for medical personnel on a display unit 24, e.g., on at least one monitor, of the user interface 23. In addition, the user interface 23 includes an input unit 25 by which information and/or parameters may be entered by medical personnel during a scanning process.

The magnetic resonance device 10 further includes a local coil 200 disposed directly on the patient 15. The local coil 200 incorporates a magnetic resonance antenna for use in conjunction with the magnetic resonance device 10, as shown by way of example in the following figures. The magnetic resonance antenna may be configured to receive magnetic resonance signals and/or transmit radiofrequency signals.

Figure 2:
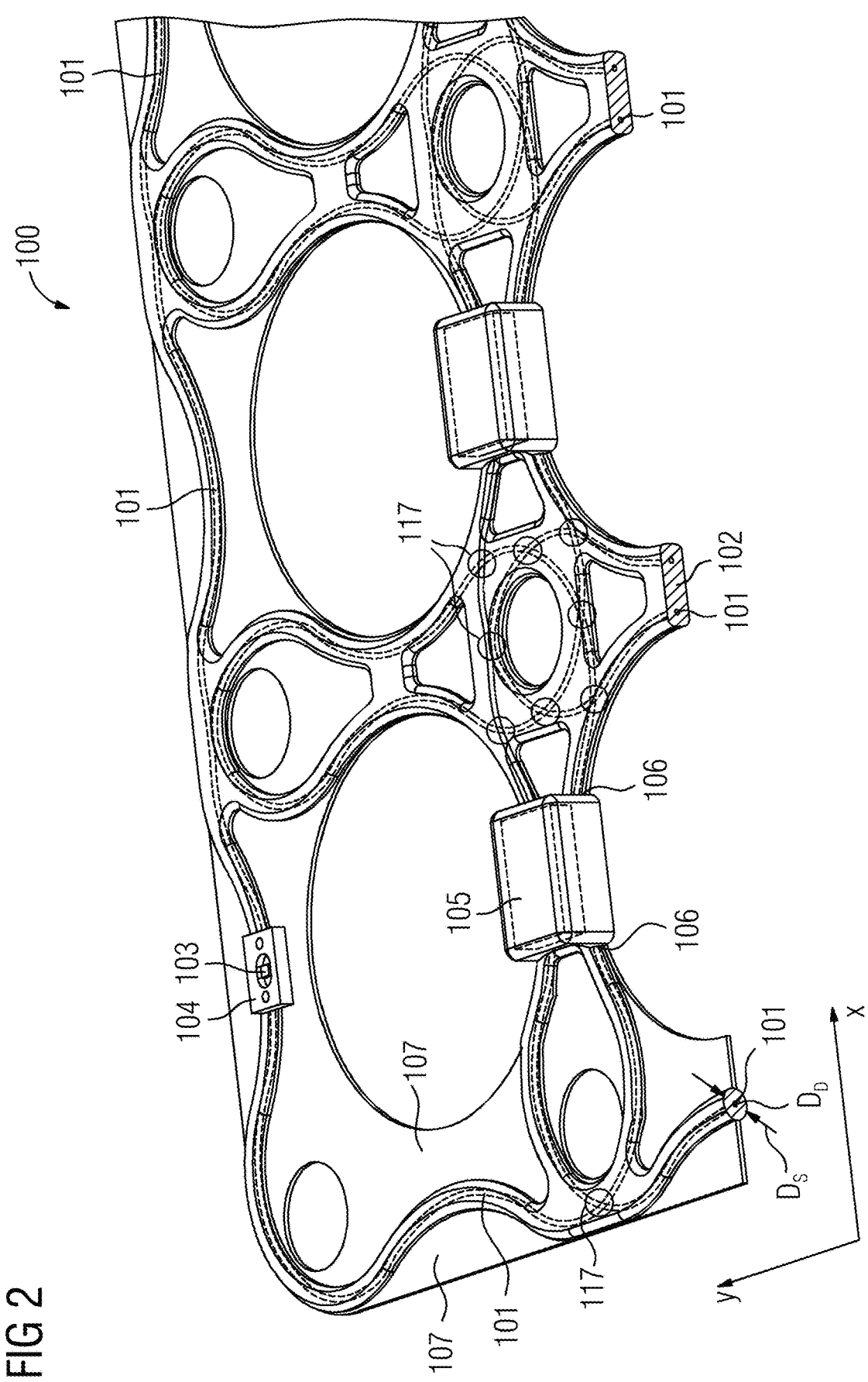
FIGS. 2, 3, and 4 depict various representations of possible magnetic resonance antennas according to embodiments.

FIG. 2 depicts a magnetic resonance antenna 100 including a plurality of wire structures 101 shaped such that an electrical voltage may be induced in each of them by a magnetic resonance signal. The wire structures 101 are completely embedded in an accommodating body 102 made of a foam material. The wire structures 101 include a diameter $D_D$. The accommodating body 102 keeps the wire structures in their shape and/or serves to provide a defined safe distance from the patient 15.

The wire structure 101 shown on the upper left includes a shortening capacitor 103 that is disposed on a circuit board 104. However, no circuit board may be used, but that the wire structure 101 is merely broken and the break point is electrically and mechanically protected by a heat shrink tube.

In addition, an electronic component 105 is disposed on the magnetic resonance antenna 100. This may be connected, for example, via a unit that is fixedly connected to the accommodating body 102.

The accommodating body 102 extends planarly in an x-y plane if the magnetic resonance antenna 100 is laid out flat. The accommodating body 102 includes two opposing surfaces, with the wire structures 101 disposed centrally between the opposing surfaces.

In the immediate vicinity of the wire structure, the magnetic resonance antenna is made thicker than in regions 107 remote from the wire structures 101 along the x-y plane, i.e., regions of the accommodating body 102 farther away from the wire structures 101. In the regions 107, the magnetic resonance antenna 100, for example the accommodating body 102, is made comparatively thin. The regions 107 may therefore also be referred to as membrane regions, since the regions 107 include a large planar extent, in this case in the x-y plane, in relation to their thickness.

The regions of the accommodating body 102 around the wire structures 101 may have a lower density than the regions 107 remote from the wire structures. For example, the regions 107 may be made of a more compressed foam material than the regions around the wire structures 101. The regions 107 are used to maintain the shape of the magnetic resonance antenna 100.

Figure 3:
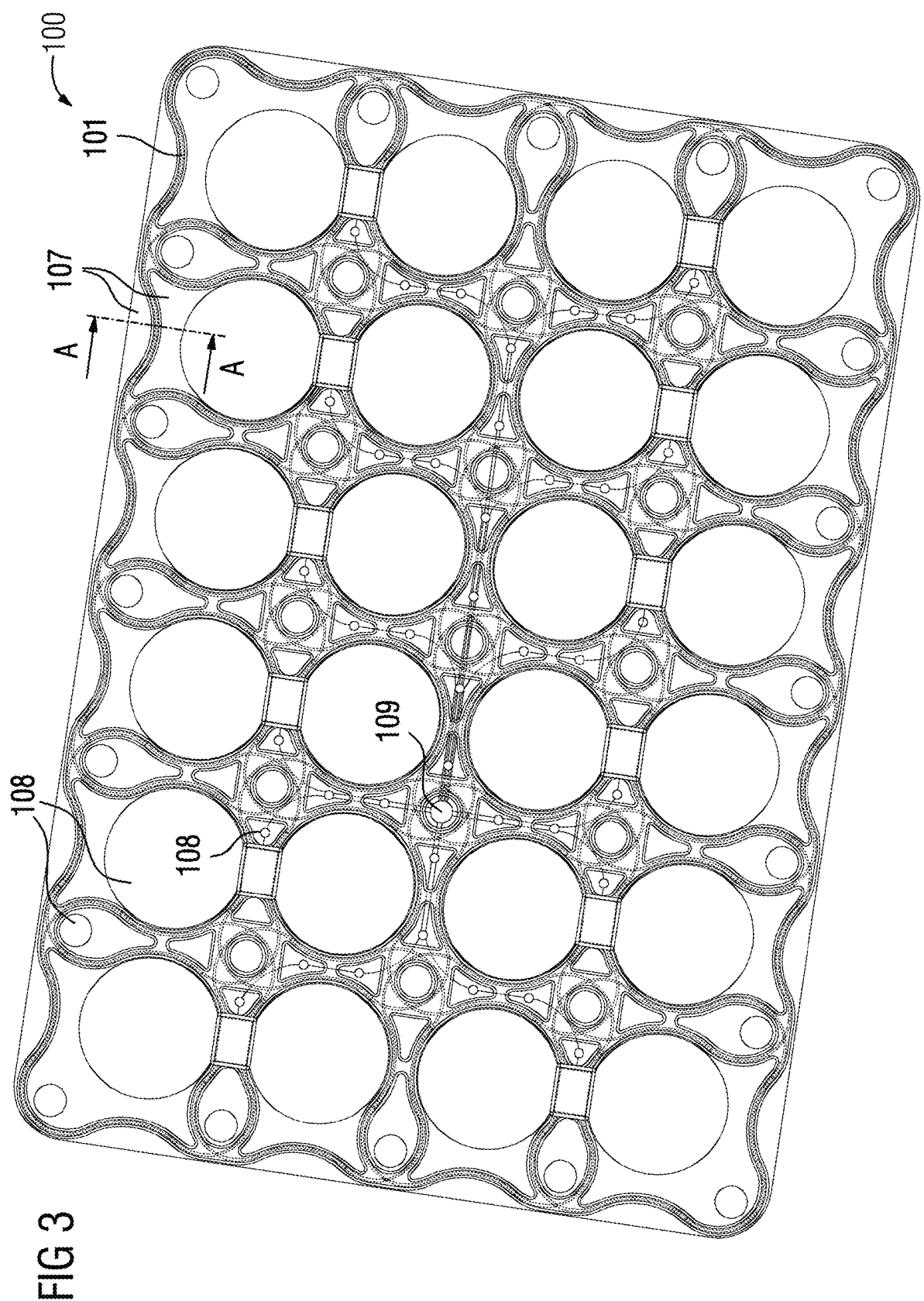

As may also be seen in FIG. 3, the regions of the accommodating body remote from the wire structures include a plurality of apertures 108, for example cutouts and/or holes. The smaller apertures 108 may be useful for fixing the magnetic resonance antenna 100 to other parts, for example other layers, of the local coil 200, for example using snap fasteners or Velcro areas, etc.

In addition, smaller apertures 108 are useful for routing cables within the local coil 200; cables may be threaded through the small apertures from one side of the accommodating body 102 to the other side of the accommodating body 102 such that such a cable may be disposed partially on one side and partially on the other side of the accommodating body 102.

In addition, the apertures 108 are configured to increase the flexibility of the magnetic resonance antenna 100. The larger apertures 108 may be suitable for providing openings to an outer skin of the local coil 200.

The magnetic resonance antenna also includes an antenna terminal 109 for connecting the magnetic resonance antenna 100 to an interface, for example a signal transmission cable, of the local coil 200.

Figure 4:
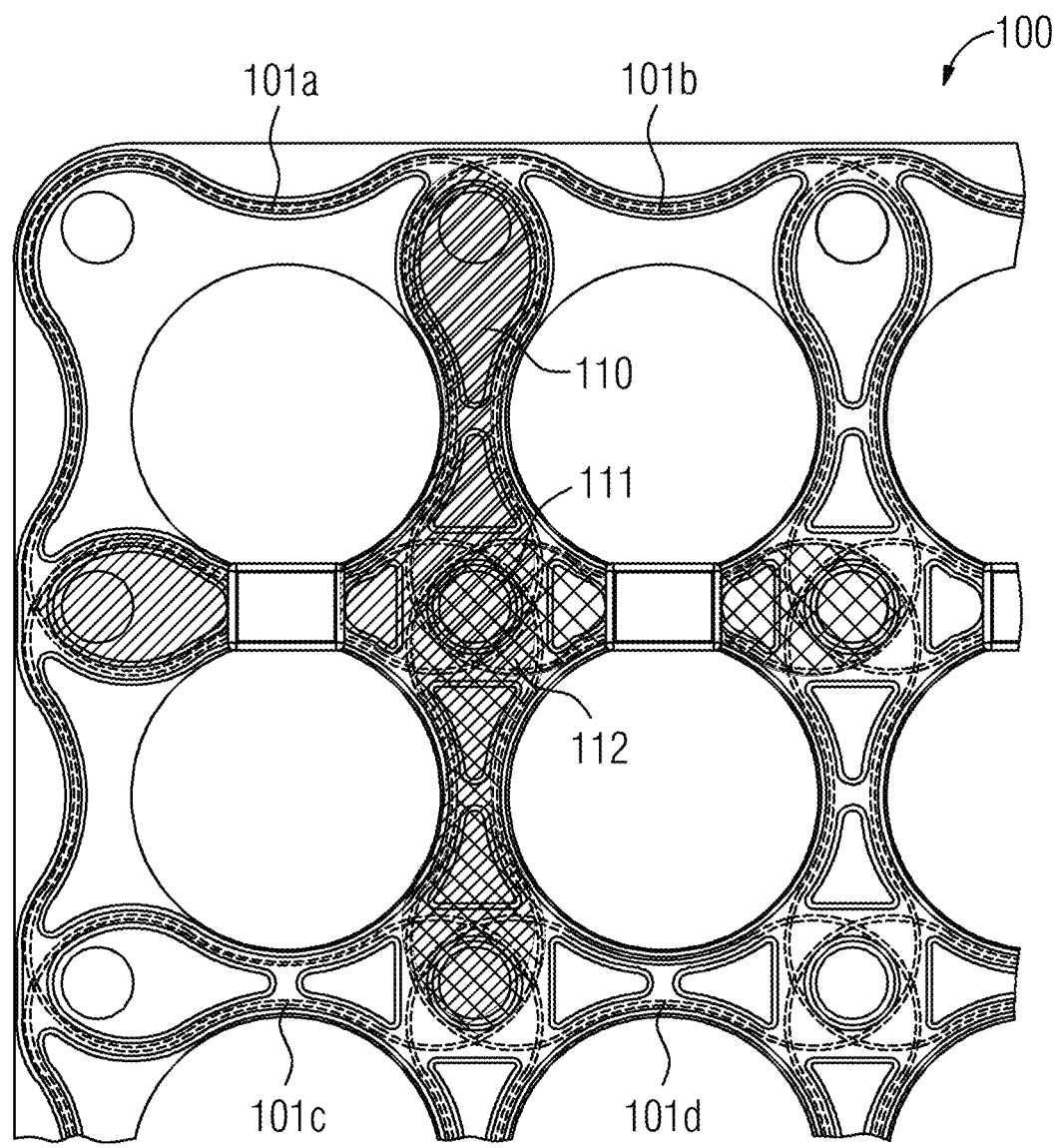

The wire structures 101 fixed in the accommodating body 102 may be formed into a wide variety of shapes. FIG. 4 depicts possible shapes and the associated overlap regions 110, 111, 112 of the wire structures 101a, 101b, 101c, 101d. For example, the overlap region 110 of the wire structures 101a and 101b, the overlap region 112 of the wire structures 101c, 101b and 101d, and the overlap region 111 of the wire structures 101a, 101b, 101c and 101d are shown.

Figure 5:
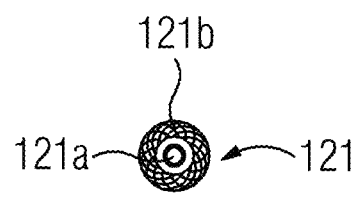
FIG. 5 depicts cross-sectional representations of possible wire structures of a magnetic resonance antenna according to an embodiment.
Figure 5:
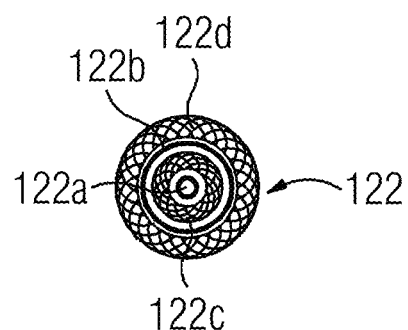
Figure 5:
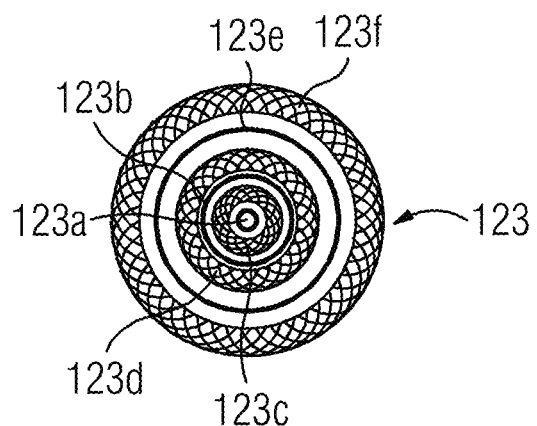
Figure 5:
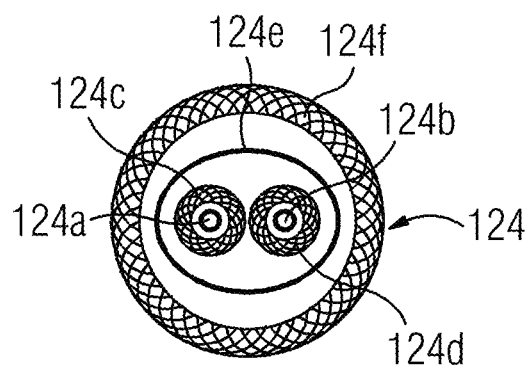

FIG. 5 depicts cross-sections of various types of electrical lines that may be used in the wire structures 101. The line type 121 is a single electrical conductor made of an electrically conductive material 121a surrounded by an insulating material 121b as a cable sheath. The line type 122 is a coaxial electrical line, i.e., a line including two coaxially arranged conductive materials 122da, 122b between which a dielectric 122c is disposed, and another insulating material 122d as a cable sheath. The line type 123 is a triaxial electrical line including three coaxially arranged conductive materials 123a, 123b, 123e, between each of which a dielectric 123c, 123d is disposed, and a further insulating material 123f as a cable sheath. The conductor type 124 is a sheathed multiple electrical line including two electrically conductive materials 123a, 123b disposed side by side, each sheathed by an insulating material 123c, 123d so as to be electrically insulated from one another; these are in turn surrounded by another electrically conductive material 123e and another insulating material 124f as a cable sheath.

By using such types of lines in the wire structures 101, very good values may be achieved for the magnetic resonance antenna 100 in terms of dielectric strength and mechanical resilience. They are available by the meter and do not require photochemical processing, but may be embedded in a foam in which, for example, a slit having the desired shape of the wire structure 101 has previously been made.

Figure 6:
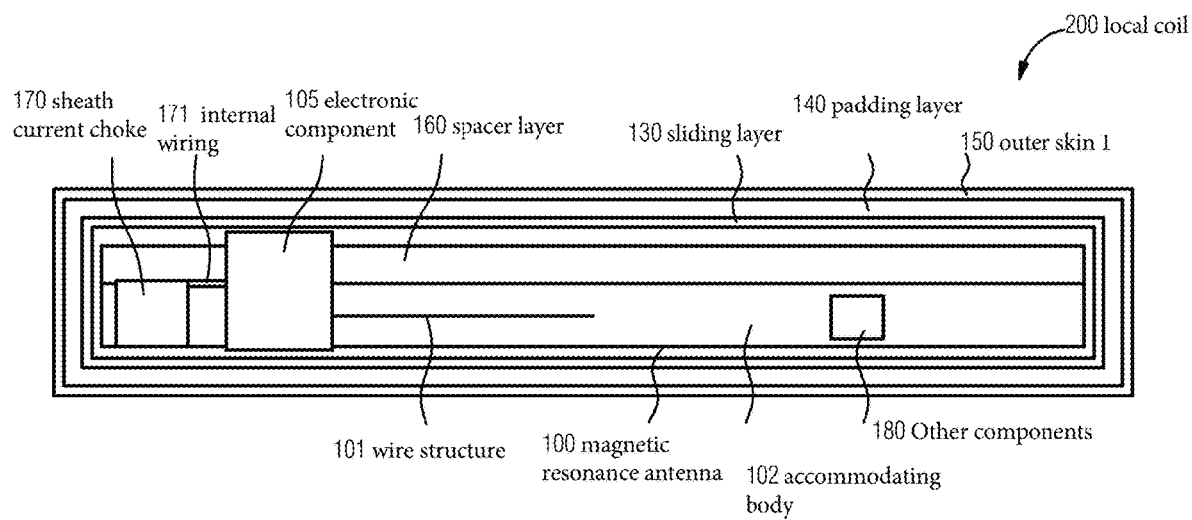
FIG. 6 depicts a possible structure of a local coil with a magnetic resonance antenna according to an embodiment.

FIG. 6 depicts a typical structure of a local coil 200. It includes a magnetic resonance antenna 100 including an accommodating body 102 made of foam material and a wire structure 101 embedded therein. Here it also includes an electronic component 105 such as e.g., a preamplifier for amplifying the magnetic resonance signals received by the wire structure 101. For example, the electronic component 105 may include a rigid housing.

The local coil 200 also includes internal wiring 171 that may be threaded through the accommodating body 102, for example through apertures 108 in the accommodating body 102 at some locations. In this example, the internal wiring establishes a connection to a sheath current choke 170. The local coil 200 also includes a spacer layer 160 that provides height leveling of the electronic component 105. Other components 180 of the local coil 102 may be embedded in the accommodating body 102.

The hitherto described internal parts of the local coil 200 shown in FIG. 6 are enclosed from inside to out by three layers: a sliding layer 130, a padding layer 140, and an outer skin 150. The internal parts are not fixedly connected to the sliding layer 130 so that they may slide within it.

Figure 7:
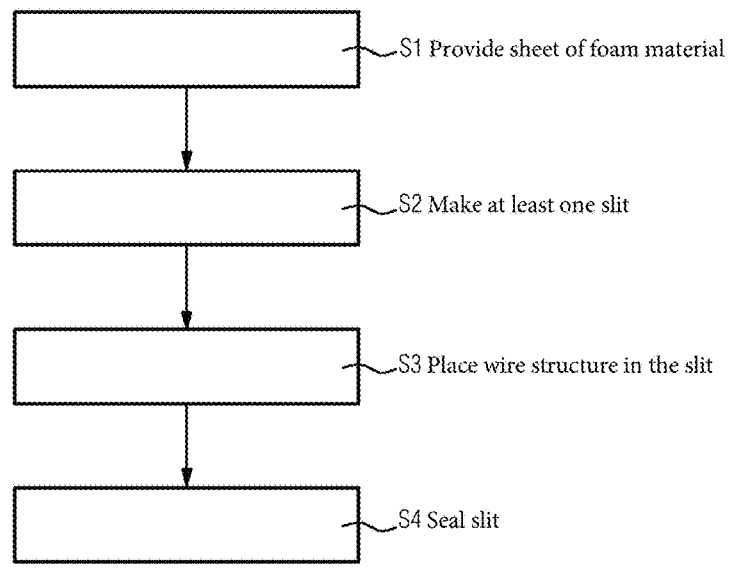
FIG. 7 depicts a flowchart of a method for producing a magnetic resonance antenna according to an embodiment.
Figure 8:
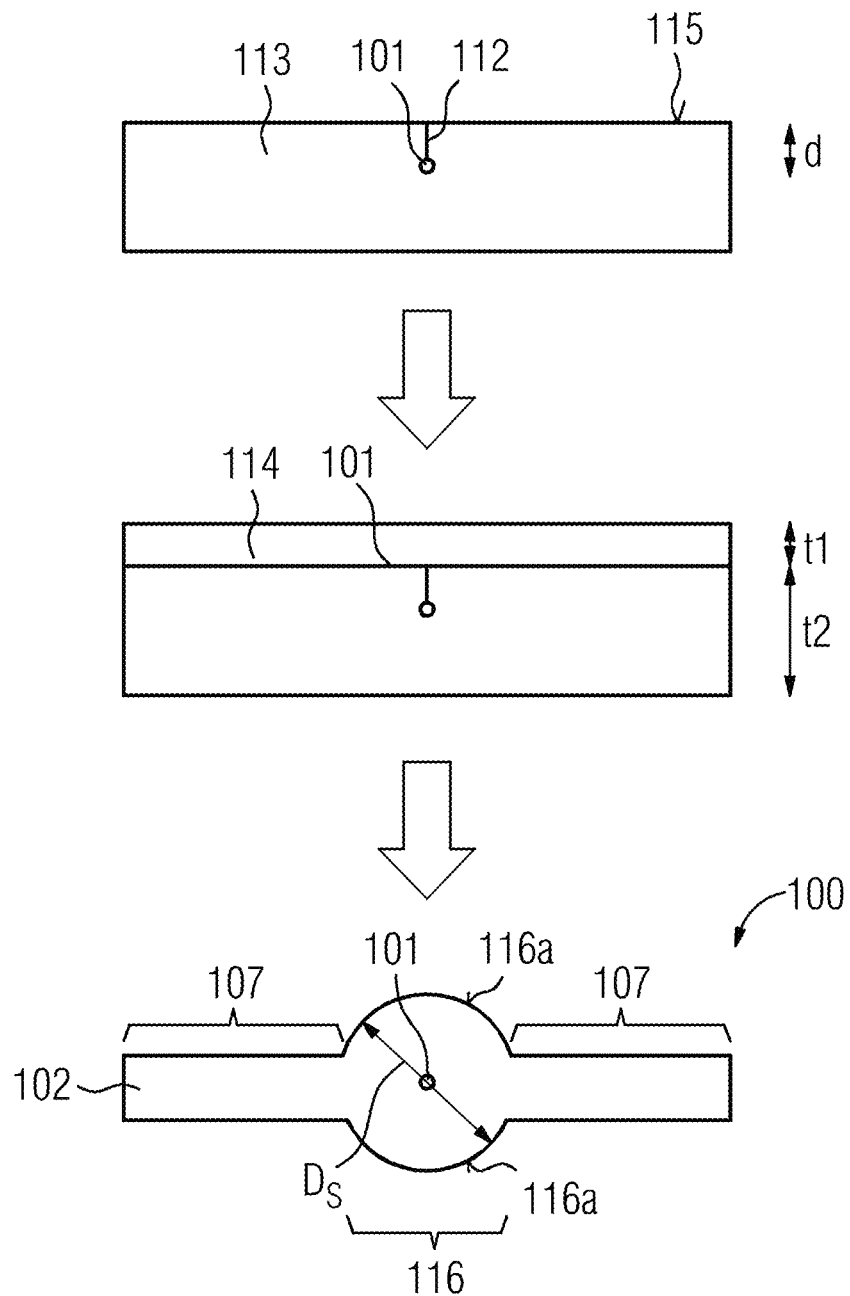
FIG. 8 depicts different stages in the production of a magnetic resonance antenna according to an embodiment.

FIG. 7 schematically depicts a method for producing a magnetic resonance antenna, including the steps S1 to S4. In S1, a sheet of foam material is provided. FIG. 8 depicts such a provided sheet 113 that may for example have a thickness t2 of between 5 and 15 mm.

In S2, at least one slit is made in the sheet. The at least one slit may be made, for example, using a scalpel, a punching knife, and/or a laser. Such a slit 112 is shown in FIG. 8. The slit 112 is made on a surface 115 of the sheet 113.

In S3, at least one wire structure 101 is placed in the at least one slit. After placement, the at least one wire structure is held in place by the foam material surrounding it. Such a placed wire structure 101 is shown in FIG. 8. The position of the wire structure 101 may be adjusted depending on the slit depth d. A liner 114 of foam material may be applied to the surface 115, as shown in the middle section of FIG. 8. For example, the liner 114 may include a thickness t1 of between 1 and 8 mm, for example between 2 and 5 mm.

For example, the sheet 113 may have a thickness t2 of 8 mm, the liner may have a thickness t1 of 2 mm, and the slit may have a depth d of 4 mm. Taking into account the thickness of the wire structure of e.g., 2 mm, the wire structure may be located centrally between the upper surface of the liner 114 and the lower surface of the sheet 113.

In S4, pressure and/or temperature is applied to the sheet so that the at least one slit is sealed. The thermostamping step results in the structure shown in the lower section of FIG. 8. The liner 114 and sheet 113 have combined to form an ideally homogeneous accommodating body 102. The wire structure is centered between opposing surfaces 116a and 116b of the accommodating body 102.

The accommodating body 102 has different thicknesses depending on the distance from the wire structure 101: in an area 116 around the wire structure 101 with a diameter $D_S$, the accommodating body 102 is thicker than in the areas 107 farther away from the wire structure 101. In step S4, the areas 107 have been more heavily compressed so that they also have a higher density.

For example, after the thermostamping step, the maximum thickness of the magnetic resonance antenna 110 in the area 116 is compressed from 10 to 8 mm and holds the wire structure 101 in the center. In the areas 107, the magnetic resonance antenna 100 is compressed from an initial thickness of 10 mm to a thickness of 1 to 4 mm, for example.

The previously applied liner 114 may reduce the risk of the slit 112 gaping open and exposing the wire structure 101 after applying pressure and/or temperature.

As may be seen in FIG. 2, this production method may also be used to create overlapping wire structures that cross at intersection points 117. Shortening capacitors 103, for example, previously incorporated into the wire structure 101 may also be encased in the foam. For any electronic components 105, a framework or an underside of an electronics housing for example may be co-impressed in the foam to create a tight bond between wire structures 101 receiving magnetic resonance signals and the electronics.

The methods described in detail above, as well as the magnetic resonance antenna, local coil and magnetic resonance device illustrated, are merely embodiments that may be modified in a variety of ways by persons skilled in the art without departing from the scope of the invention. Moreover, the use of the indefinite articles "a" or "an" does not preclude the features in question from being present more than once. Similarly, the term "unit" does not preclude the components in question from including a plurality of interacting sub-components that may also be spatially distributed.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that the dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A magnetic resonance antenna comprising:
   at least one wire structure shaped such that an electrical voltage may be induced in the at least one wire structure by a magnetic resonance signal; and
   at least one accommodating body in which the at least one wire structure is embedded completely, wherein the at least one accommodating body includes regions close to the at least one wire structure that have a lower density than regions remote from the at least one wire structure.

2. The magnetic resonance antenna as claimed in claim 1, wherein the at least one accommodating body consists of at least one of a foam material, a felt material, or a knitted fabric.

3. The magnetic resonance antenna of claim 1, wherein the at least one wire structure comprises at least one of a single electrical line, a coaxial electrical line, a triaxial electrical line, or a sheathed multiple electrical line.

4. The magnetic resonance antenna of claim 1, wherein the at least one wire structure comprises at least one capacitor.

5. The magnetic resonance antenna of claim 1, wherein the magnetic resonance antenna comprises at least one component that is fixedly connected to the at least one accommodating body, for connecting an electronic component.

6. The magnetic resonance antenna of claim 1, wherein the at least one accommodating body is planar and includes two opposing surfaces, wherein the at least one wire structure is disposed centrally between the two opposing surfaces.

7. The magnetic resonance antenna of claim 1, wherein the regions of the at least one accommodating body remote from the at least one wire structure include at least one aperture.

8. A local coil comprising:
   at least one magnetic resonance antenna comprising:
      at least one wire structure shaped such that an electrical voltage may be induced in the at least one wire structure by a magnetic resonance signal; and
      at least one accommodating body in which the at least one wire structure is embedded completely, wherein the at least one accommodating body includes regions close to the at least one wire structure that have a lower density than regions remote from the at least one wire structure.

9. The local coil of claim 8, further comprising:
   an outer skin, wherein the at least one accommodating body including the at least one wire structure embedded therein is enclosed by the outer skin.

10. The local coil of claim 8, wherein the at least one wire structure is flexible, the at least one accommodating body is flexible, or the at least one wire structure and the at least one accommodating body is flexible.

11. The local coil of claim 8, wherein the at least one wire structure comprises a shortening capacitor.

* * * * *